(12) United States Patent
Nummela

(10) Patent No.: US 8,360,578 B2
(45) Date of Patent: Jan. 29, 2013

(54) EYE TRACKER DEVICE

(75) Inventor: Ville Nummela, Helsinki (FI)

(73) Assignee: Nokia Corporation, Espoo (FI)

( * ) Notice: Subject to any disclaimer, the term of this patent is extended or adjusted under 35 U.S.C. 154(b) by 520 days.

(21) Appl. No.: 12/223,245

(22) PCT Filed: Jan. 26, 2006

(86) PCT No.: PCT/FI2006/050043
§ 371 (c)(1),
(2), (4) Date: Jan. 21, 2011

(87) PCT Pub. No.: WO2007/085682
PCT Pub. Date: Aug. 2, 2007

(65) Prior Publication Data
US 2011/0109880 A1 May 12, 2011

(51) Int. Cl.
*A61B 3/14* (2006.01)
(52) U.S. Cl. .................. 351/209; 351/221; 351/246
(58) Field of Classification Search ............. 351/209, 351/210, 211, 221, 246; 382/103
See application file for complete search history.

(56) References Cited

U.S. PATENT DOCUMENTS

| 3,712,716 A | 1/1973 | Cornsweet et al. |
| 4,836,670 A | 6/1989 | Hutchinson |
| 5,100,227 A | 3/1992 | Winocur |
| 5,270,748 A | 12/1993 | Katz |
| 5,428,413 A | 6/1995 | Shindo |
| 5,481,622 A | 1/1996 | Gerhardt et al. |
| 5,907,722 A | 5/1999 | Suzuki |
| 6,580,529 B1 | 6/2003 | Amitai et al. |
| 7,130,447 B2 * | 10/2006 | Aughey et al. ............ 382/103 |
| 2004/0062502 A1 | 4/2004 | Levola |

FOREIGN PATENT DOCUMENTS

| EP | 0821908 | 2/1998 |
| EP | 0942350 | 9/1999 |
| EP | 1336372 | 8/2003 |
| WO | WO 2004/045399 | 6/2004 |
| WO | WO 2004/055556 | 7/2004 |

OTHER PUBLICATIONS

Office Action from Chinese Patent Application No. 200680051822.6, mailed Jun. 23, 2011.

* cited by examiner

*Primary Examiner* — Hung Dang
(74) *Attorney, Agent, or Firm* — Alston & Bird LLP

(57) ABSTRACT

Two collimated light beams are directed towards an eye to provide two reflection spots. The collimated light beams are advantageously provided by a diffractive beam expander. The reflection spots and the pupil of the eye are monitored by an imaging unit. The collimated beams are at different angles with respect to the imaging unit. The gaze direction is determined based on the angles, the positions of the reflections spots, and the position of the pupil. Thanks to the use of the two collimated beams, the detected gaze direction is substantially independent of the size of the eye, independent of the lateral position of the eye, and independent of the distance between the imaging unit and the eye. The detected gaze angle may be used for selecting between options displayed by a virtual display.

35 Claims, 15 Drawing Sheets

EYE TRACKER DEVICE

CROSS REFERENCE TO RELATED APPLICATIONS

This application is the U.S. National Stage of International Application Number PCT/FI2006/050043 filed on Jan. 26, 2006 which was published in English on Aug. 2, 2007 under International Publication Number WO 2007/085682.

FIELD OF THE INVENTION

The present invention relates to the determination of the gaze direction of an eye.

BACKGROUND OF THE INVENTION

The gaze direction of a person may be used to select options displayed on a computer screen. Thus, an eye tracker device providing information on the gaze direction may be used, for example, as a pointing and selecting device instead of a computer mouse.

When light impinges on the eye, several reflections occur on the boundaries of the lens, cornea and retina. These reflections provide reflection spots known as the Purkinje images. The reflection from the outer corneal surface provides the first Purkinje image, also called as the glint. The orientation of the eye may be determined based on the position of the pupil with respect to the position of the first Purkinje image.

U.S. Pat. No. 4,836,670 discloses an eye movement detector, which utilizes an infrared-emitting diode mounted coaxially in front of the lens of an infrared-sensitive camera for acquiring an image of the eye. The reflected light causes a glint from the surface of the cornea. The image of the eye is analyzed to determine the location of the pupil's center and the location of the glint relative to each other and this information is used to determine the gaze direction.

SUMMARY OF THE INVENTION

The object of the present invention is to provide a method for determining the gaze direction. The object of the present invention is also to provide an eye tracker device for determining gaze direction. A further object of the present invention is to provide a portable device which comprises an eye tracker device. The object of the present invention is also to provide a computer program product implementing said method.

According to a first aspect of the present invention, there is a device for detecting gaze direction of an eye, said device comprising at least:
  an imaging unit to acquire an image of said eye,
  at least one illuminating unit to provide a first substantially collimated light beam and a second substantially collimated light beam, said collimated light beams having different directions with respect to said device such that said first collimated light beam provides a first reflection spot when light is reflected from the surface of the eye and that said second collimated light beam provides a second reflection spot when light is reflected from the surface of the eye, said reflection spots appearing in said image, and
  a data processing unit to determine the gaze direction of the eye with respect to said device based on the position of said first reflection spot in said image, on the position of said second reflection spot in said image, on the position of the pupil and/or iris of the eye in said image, and on the directions of the collimated light beams.

According to a second aspect of the present invention, there is a method for detecting gaze direction of an eye, said method comprising at least:
  directing a first substantially collimated light beam towards the eye in order to provide a first reflection spot when light is reflected from the surface of the eye,
  directing a second substantially collimated light beam towards the eye in order to provide a second reflection spot when light is reflected from the surface of the eye, said second collimated light beam having a direction different from the direction of said first collimated light beam,
  acquiring an image of the eye by an imaging unit,
  determining the gaze direction of said eye with respect to said imaging unit based on the position of said first reflection spot in said image, on the position of said second reflection spot in said image, on the position of the pupil and/or iris of the eye in said image, and on the directions of the collimated light beams.

According to a third aspect of the present invention, there is a portable device comprising an eye tracking device for detecting gaze direction of an eye, said tracking device comprising at least:
  an imaging unit to acquire an image of said eye,
  at least one illuminating unit to provide a first substantially collimated light beam and a second substantially collimated light beam, said collimated light beams having different directions with respect to said device such that said first collimated light beam provides a first reflection spot when light is reflected from the surface of the eye and that said second collimated light beam provides a second reflection spot when light is reflected from the surface of the eye, said reflection spots appearing in said image, and
  a data processing unit to determine the gaze direction of the eye with respect to said tracking device based on the position of said first reflection spot in said image, on the position of said second reflection spot in said image, on the position of the pupil and/or iris of the eye in said image, and on the directions of the collimated light beams.

According to a fourth aspect of the present invention, there is a computer program product for determining the gaze direction of an eye based on data provided by a system comprising:
  an imaging unit to acquire an image of said eye, and
  illuminating means to provide a first substantially collimated light beam and a second substantially collimated light beam, said collimated light beams having different directions with respect to said imaging unit such that said first collimated light beam provides a first reflection spot when light is reflected from the surface of the eye and that said second collimated light beam provides a second reflection spot when light is reflected from the surface of the eye, said reflection spots appearing in said image,
  said computer program product comprising computer program code sections stored in a readable medium, which when executed by a processor are for determining the gaze direction of said eye with respect to said imaging unit based on the position of said first reflection spot in said image, on the position of said second reflection spot in said image, on the position of the pupil and/or iris of the eye in said image, and on the directions of the collimated light beams.

The determination of the gaze direction is substantially independent of the distance between the eye and the tracker device. The determination is also substantially independent of the lateral movement of the eye, and of the size of the eye. Thus, the eye may be moved within a large area, i.e. the position of the tracker device does not need to be fixed with respect to the observer's head.

The embodiments of the invention and their benefits will become more apparent to a person skilled in the art through the description and examples given herein below, and also through the appended claims.

BRIEF DESCRIPTION OF THE DRAWINGS

In the following examples, the embodiments of the invention will be described in more detail with reference to the appended drawings in which.

DETAILED DESCRIPTION

Figure 1:
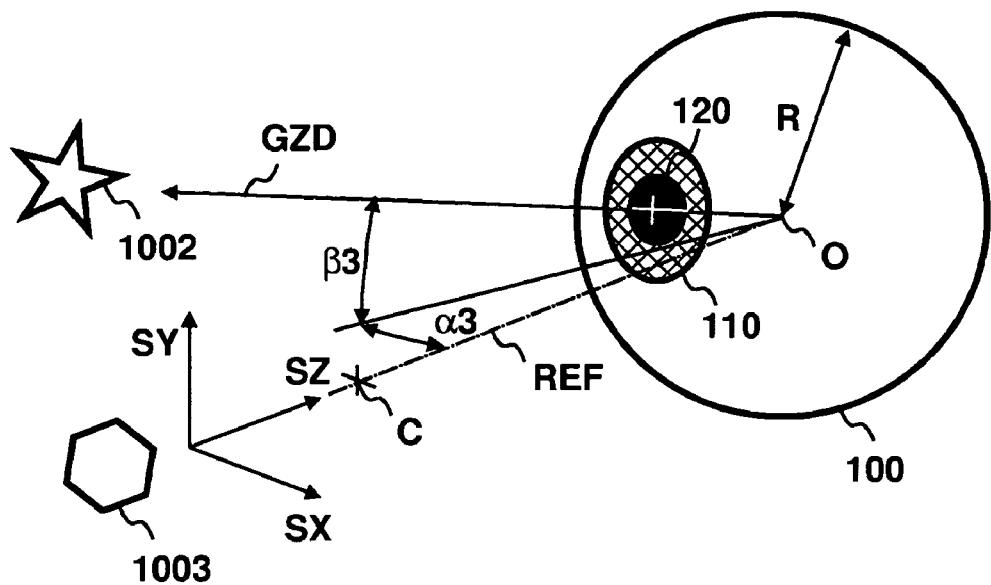
FIG. 1 shows schematically the gaze direction with respect to a reference coordinate system.

Referring to FIG. 1, the gaze direction GZD of the eye 100 may be defined by a horizontal gaze angle $\alpha 3$ and a vertical gaze angle $\beta 3$ with respect to the direction SZ of a reference coordinate system. The direction SY defines the vertical direction, and the direction SX defines the horizontal direction of the reference coordinate system.

The actual form of the eye 100 is slightly non-spherical, but the form of the cornea may be approximated by a spherical surface. Herein, the center O of the eye 100 refers to the center of a best-fit sphere, said sphere being fitted with the corneal surface. Herein, the radius R of the eye 100 refers to the radius of said best-fit sphere.

The gaze direction GZD is defined by a line passing through the center O of the eye 100 and the best-fit center of the pupil 120. The pupil 120 is surrounded by the iris 110. The determination of the best-fit center of the pupil may also be determined partly or completely based on the location of the iris 110.

A reference line REF is parallel to the direction SZ of the reference coordinate system. The position of the eye 100 may be moved in the directions SX, SY and/or SZ. The reference line REF does not, in general, pass through the center O of the eye 100.

Objects 1002, 1003 are located at a considerable or infinite distance from the eye 100. The objects 1002, 1003 may be physical objects (e.g. bodies), images displayed on a remote display screen, or virtual images displayed by a virtual display.

It is assumed that the angular coordinates of the objects 1002 and 1003 are known with respect to a point C on the reference line REF, and that the distance between the eye 100 and the objects 1002, 1003 is great when compared to the distance between the point C and the eye center O. The ratio of the distances may be e.g. greater than or equal to ten. Thus, the objects 1002, 1003 may be associated with gaze directions. Consequently, by knowing the gaze angles $\alpha 3$ and $\beta 3$, it may be determined which object the eye 100 is looking at, i.e. whether the eye 100 is looking at the star 1002 or the hexagon 1003.

Figure 2:
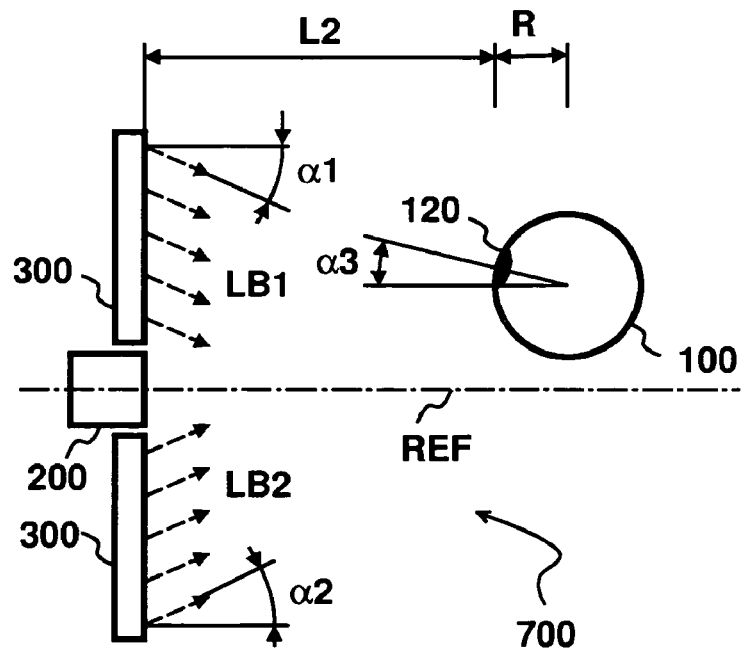
FIG. 2 shows schematically an eye tracking device for determining the gaze direction.

Referring to FIG. 2, the gaze angles $\alpha 3$ and $\beta 3$ are determined by an eye tracker device 700 which comprises one or more illumination units 300 and an imaging unit 200 (only the horizontal angle $\alpha 3$ is shown in FIG. 2). The illumination units 300 provide at least two substantially collimated light beams LB1, LB2 which are directed towards the eye 100, and which beams LB1, LB2 have different directions. The imaging unit 200 provides an image of the eye 100.

The direction of the first collimated beam LB1 may be identified by a horizontal angle α1 and a vertical angle β1 between the beam LB1 and the reference line REF. The direction of the second collimated beam LB2 may be identified by a horizontal angle α2 and a vertical angle β2 between the beam LB2 and the reference line REF (the vertical angles β1 and β2 are not shown in FIG. 2). L2 denotes the distance between the imaging unit 200 and the eye 100.

Figure 3:
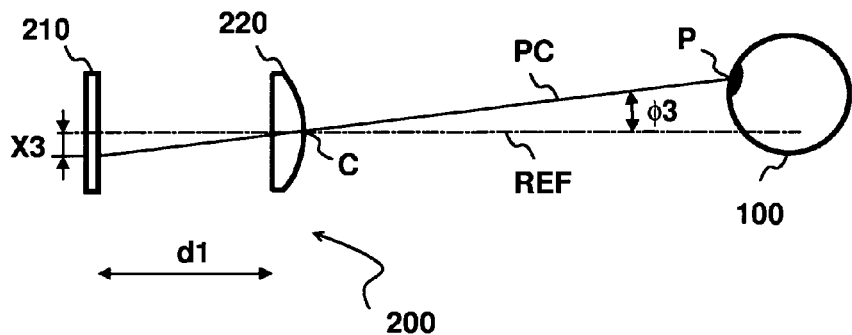
FIG. 3 shows schematically the propagation of a light ray through the imaging optics.

Referring to FIG. 3, the imaging unit 200 comprises imaging optics 220 and an image sensor 210, which may be e.g. a charge coupled device (CCD). The distance d1 between the imaging optics 220 and the image sensor 210 is known, and thus the pixels of the image sensor 210 may be associated with the angular positions of the respective features. For example, the pupil center P is projected to a pixel having a horizontal coordinate X3. The angle φ3 between the reference line REF and the line PC from the pupil center P to the principal point C of the imaging optics 220 may be determined based on the coordinate X3 of the respective pixel.

The imaging unit 200 may comprise means for automatic focusing. The non-ideal properties of the imaging optics 220 may cause geometric distortion of the image 201. The distortion may be corrected optically and/or by signal processing.

Figure 4:
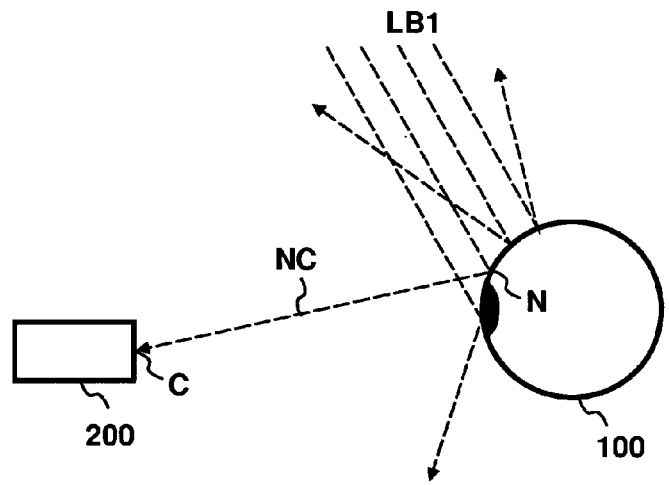
FIG. 4 shows schematically reflection of light rays from the corneal surface.

Referring to FIG. 4, the light beam LB1 is reflected from the corneal surface providing a plurality of reflected rays, which propagate in several different directions. A narrow fan of reflected light rays is received by the aperture of the imaging unit 200. Said fan is herein represented by a single ray NC, which is the weighted-average of said fan. The ray NC is reflected from a reflection point N on the surface of the eye 100 to the principal point C of the imaging optics 220.

Figure 6:
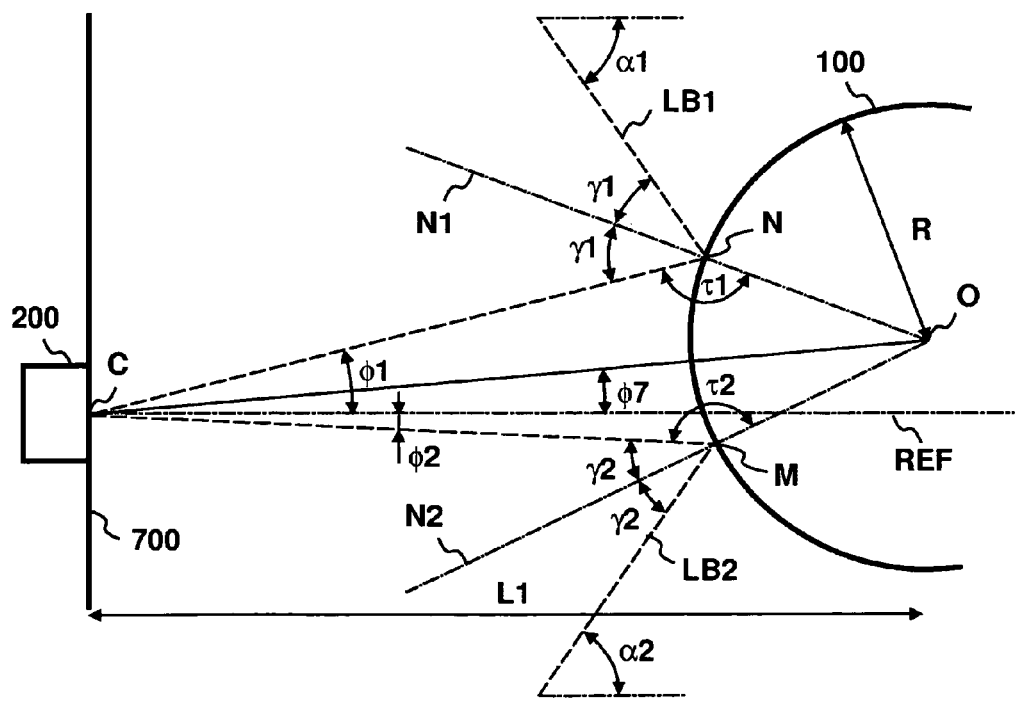
FIG. 6 is a schematic diagram showing reflection of the light rays from the corneal surface towards the imaging unit.

Also the light beam LB2 is reflected from the corneal surface towards the imaging unit 200 (not shown in FIG. 4, please see FIG. 6). The reflected rays are represented by a single ray MC, which is reflected from a reflection point M on the surface of the eye 100 to the principal point C of the imaging optics 220.

Figure 5A:
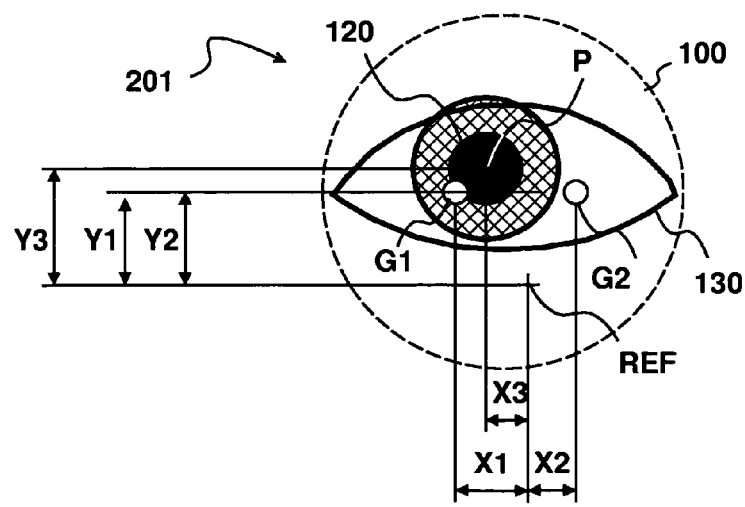
FIG. 5a shows schematically an image of the eye, said image comprising two reflection spots.

FIG. 5a shows an image 201 of the eye 100, as acquired by the imaging unit 200. The first collimated light beam LB1 is directed towards the eye 100 such that the reflection of the first beam LB1 provides a first reflection spot G1 appearing in the image 201. The second collimated light beam LB2 is directed towards the eye 100 such that the reflection of the second beam LB2 provides a second reflection spot G2 appearing in the image 201. Image analysis algorithms may be applied to determine the coordinates X1, Y1, X2, Y2 of the reflections spots G1, G2, and the coordinates X3, Y3 of the pupil P in the image 201. The reflections spots G1, G2, i.e. the first Purkinje images should be distinguished from the other Purkinje images originating from the inside of the eye 100.

When the gaze direction is changed, the pupil 120 moves with respect to the reflection spots G1, G2.

Figure 5B:
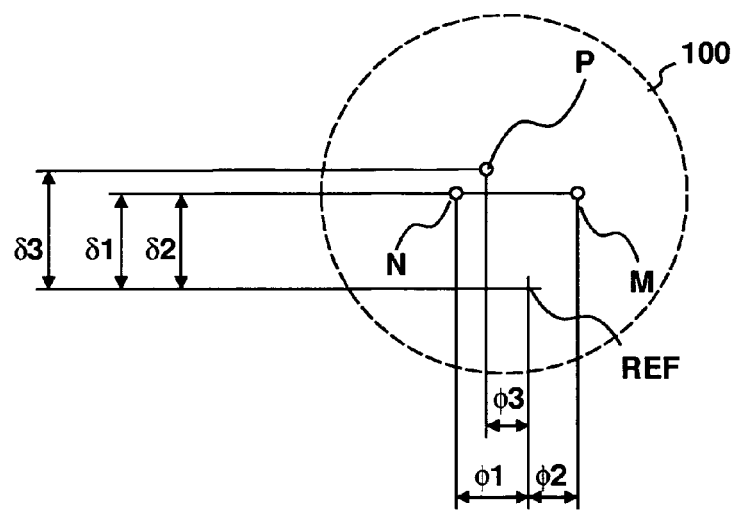
FIG. 5b shows schematically the angular positions of reflection points and the pupil center.

Referring to FIG. 5b, the angular position φ1, δ1 of the first reflection point N on the surface of the eye 100, the angular position φ2, δ2 of the second reflection point M, and the angular position φ3, δ3 of the pupil center P may be calculated on the basis of the coordinates X1, Y1, X2, Y2, X3, Y3 (FIG. 5a) according to the principle shown in FIG. 3.

The algorithm for determining the gaze direction is now first described using a simplified two-dimensional approach. Referring to FIG. 6, the light beam LB1 is reflected from the point N, and the reflected ray NC impinges on the principal point C of the optics of the imaging unit 200. The angle of incidence γ1 of the beam LB1 with respect to the surface normal N1 is equal to the angle of reflection γ1 of the light ray NC with respect to the surface normal N1. It can be found that:

$$\gamma 1 = \frac{\phi 1 + \alpha 1}{2}, \qquad (1)$$

and that:

$$\tau 1 = 180° - \frac{\phi 1 + \alpha 1}{2}. \qquad (2)$$

The light beam LB2 is reflected from a point M, and the reflected ray MC impinges on the principal point C of the imaging unit 200. The angle of incidence γ2 of the beam LB2 with respect to the surface normal N2 is equal to the angle of reflection γ2 of the light ray MC with respect to the surface normal N2. It can be found that:

$$\gamma 2 = \frac{\phi 2 + \alpha 2}{2}, \qquad (3)$$

and that:

$$\tau 2 = 180° - \frac{\phi 2 + \alpha 2}{2}. \qquad (4)$$

Two triangles, namely the triangle ONC and the triangle OMC may be identified in FIG. 6. The triangles have a common side OC, and the length of the sides ON and OM is equal to the radius R of the eye 100. The angular position φ7 of the eye center O may now be determined on the basis of the angles τ1 and τ2 using trigonometric, (e.g. the sine rule) or vector calculations.

Figure 7:
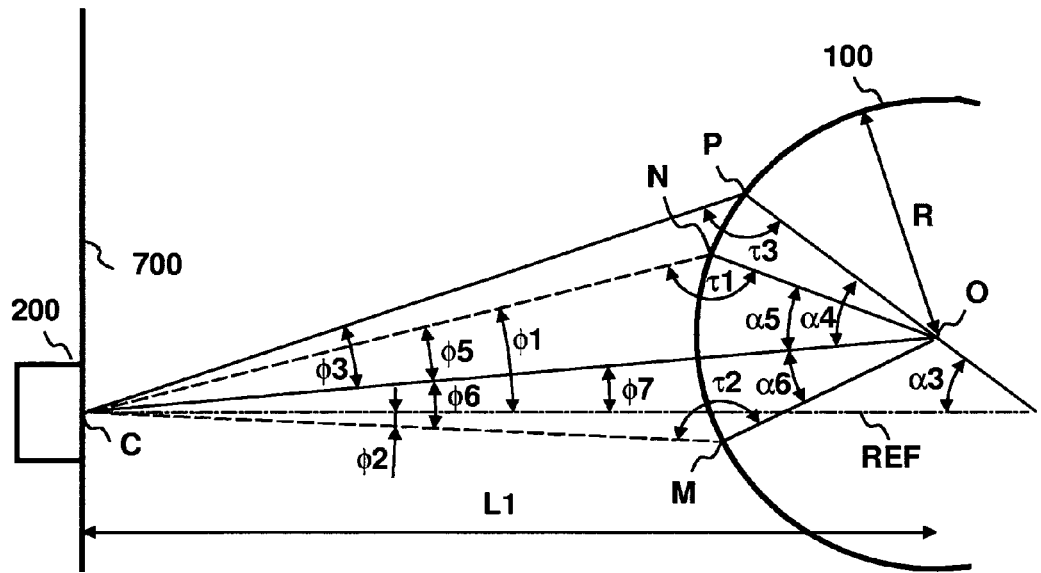
FIG. 7 is a schematic diagram showing triangles related to the determination of the gaze direction.

Referring to FIG. 7, three triangles OPC, ONC and OMC may be identified. The angles φ5 and φ6 may be calculated when the angles φ1, φ2 and φ7 are known. The point P is the center of the pupil 120. The angle α5 may now be calculated on the basis of the angles τ1 and φ5. The triangles OPC and ONC have a common side OC, and the length of the sides ON and OP is equal to the radius R of the eye 100. The angle α4 may now be determined on the basis of the angles τ1 and τ3 using trigonometric (e.g. the sine rule) or vector calculations. The horizontal gaze angle α3 may now be calculated using the angle α4 and the angular position φ7 of the eye center O.

Figure 8:
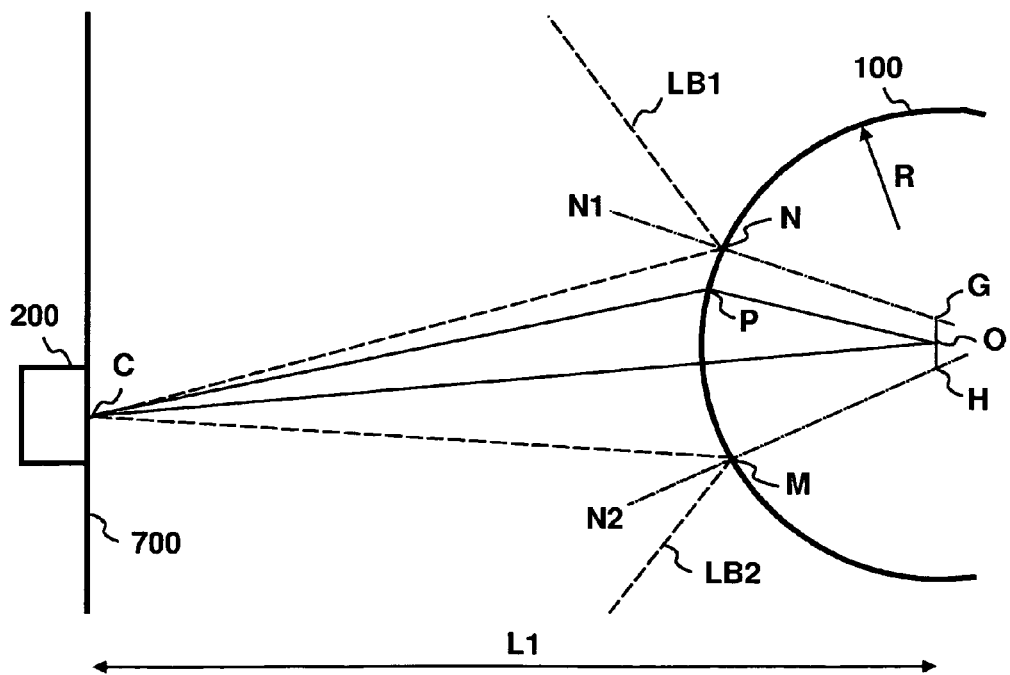
FIG. 8 is a schematic diagram showing vectors related to the determination of the gaze direction in a general three-dimensional situation.

Referring to FIG. 8, the vector OP corresponding to the gaze angles α3 and β3 of the eye 100 may be determined in a general three-dimensional situation by using vector calculations.

The first collimated beam LB1 is reflected from the point N to the principal point C of the imaging optics 200. The second collimated beam LB2 is reflected from the point M to the principal point C. At the point N the surface normal is N1 and at the point M the surface normal is N2. The direction vector of the first surface normal N1 is the average of the direction vector of the first collimated beam LB1 and the direction vector of the line CN. The direction vector of the second surface normal N2 is the average of the direction vector of the second collimated beam LB2 and the direction vector of the line CM.

It is probable that the surface normals N1, N2 do not intersect due to measurement inaccuracies and due to the slightly non-spherical form of the cornea. In that case an auxiliary vector GH may be determined to find an estimate for the eye center O. The auxiliary vector GH is the shortest possible vector connecting the surface normals N1, N2. The auxiliary vector GH is perpendicular to vectors NG and MH. The auxiliary vector GH is parallel to the cross product of the vectors NG and MG. The mid-point of the auxiliary vector GH may be used as an estimate for the eye center O. The length of the auxiliary vector GH may be used as an indication of the accuracy of the measurement.

Now, the directions of the vectors CN, NG, GH, HM and MC are known. The length of the vectors NG and HM are also known, which length is equal to the radius R of the eye 100. The remaining three unknowns, namely the lengths of the vectors CN, GH and MC may be solved based on the vector equation, which states that the five vectors must make a closed path:

$$CN + NG + GH + HM + MC = 0. \quad (5)$$

Equation (5) is written as a set of three linear equations, one equation of said set corresponding to the vector components in the direction SX (FIG. 1), one corresponding to the vector components in the direction SY, and one corresponding to the vector components in the direction SZ. There are and three unknowns and three equations, from which the unknowns may be calculated.

Now, the directions and the lengths of the vectors CN, NG, GH, HM and MC are known in terms of the eye radius R.

The position of the eye center O is approximated to be at the mid-point of the vector GH. The position of the eye center O may also be approximated by a point which is in on the vector GH. The position of the eye center O may also be approximated by a point which is in the vicinity of the vector GH.

Next, it is calculated where the line CP intersects the surface of the eye 100, which has the center O and radius R. The calculation provides two solutions. The solution corresponding to the shorter length of the vector CP is selected, as the other solution corresponds to a location on the back side of the eye 100.

The position of the eye center O and the pupil center P are now known, and the direction of the vector OP directly gives the gaze direction.

To summarize, the determination of the gaze direction comprises the following steps:
  determining the angular positions of the reflection points N, M on the surface of the eye 100 based on the coordinates of the reflection spots G1, G2 in the image 201 acquired by the imaging unit 200,
  calculating the directions of the surface normals N1, N2 at said reflection points N, M based on the directions of the collimated light beams LB1, LB2 and the directions of the vectors CN and CM,
  determining the direction of the auxiliary vector GH by calculating the cross product of the direction vectors of said surface normals N1, N2,
  calculating the lengths of the vectors CN, CM and GH,
  approximating the position of the eye center O by the mid-point of said auxiliary vector GH,
  determining the direction of the vector CP based on the coordinates of the pupil and/or iris in the image 201,
  calculating the position of the pupil center P, and
  calculating the direction of the vector OP, said direction being the gaze direction.

Figure 9:
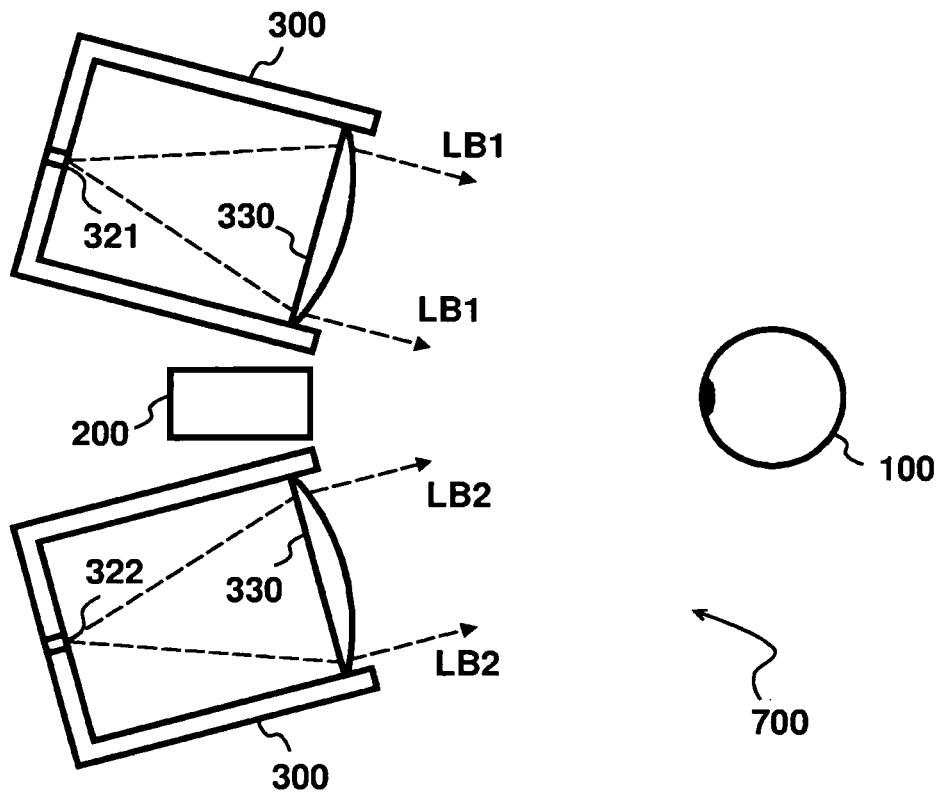
FIG. 9 shows schematically an eye tracking device comprising two illuminating units based on collimating lenses.

Referring to FIG. 9, the eye tracking device 700 may comprise two illuminating units 300 to provide the substantially collimated light beams LB1, LB2. Invisible light emitted by infrared light (IR) emitters 321, 322 is collimated by the collimating optics 330 towards the eye 100.

The collimating optics 330 of the illuminating units 300 may be optimized combinations of lenses. The collimating optics 330 may comprise Fresnel lenses. The orientation of the illuminating units 300 may be fixed or variable with respect to the imaging unit 200. The emitted light may be at a visible wavelength but pulsed such that it is substantially invisible. The emitted light may be in the UV (ultraviolet) region such that it is invisible.

Figure 10:
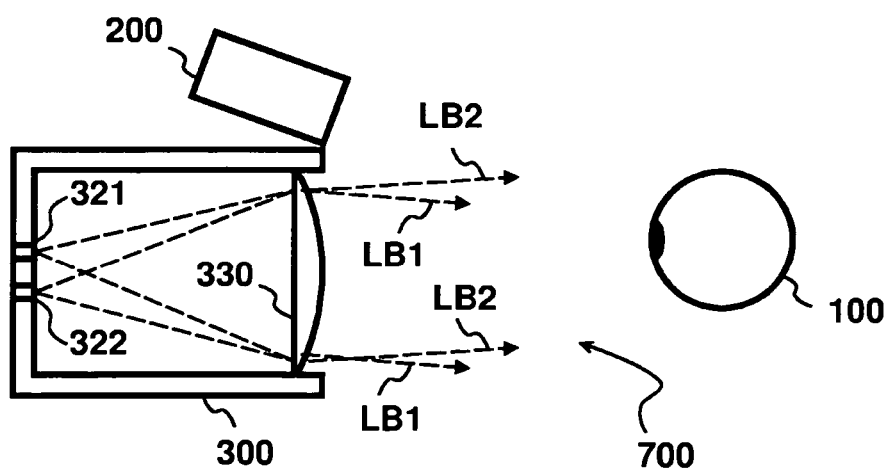
FIG. 10 shows schematically an eye tracking device comprising an illuminating unit based on collimating lenses.

Referring to FIG. 10, the eye tracking device 700 may also comprise only one illuminating unit 300 but two emitters 321, 322 to provide the substantially collimated light beams LB1, LB2.

Figure 11:
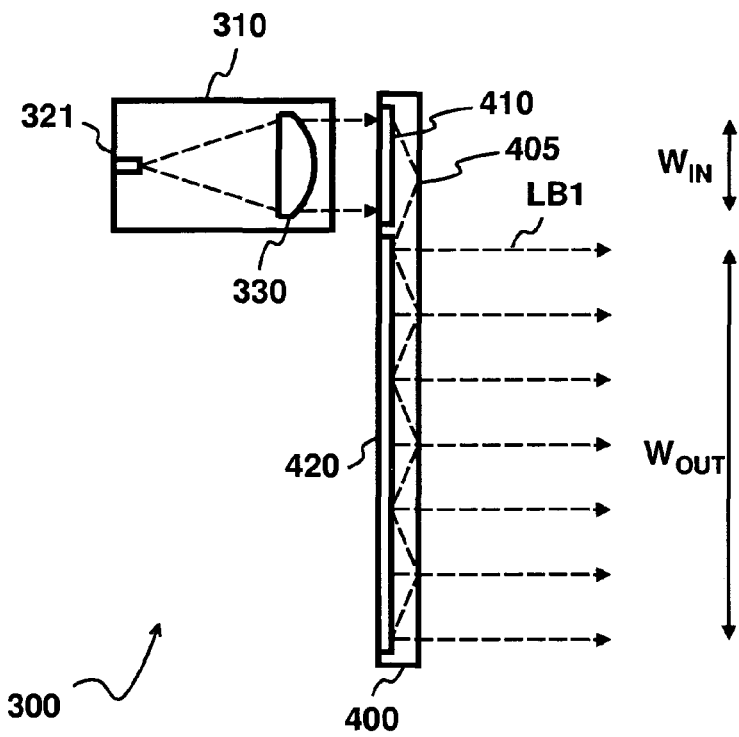
FIG. 11 shows schematically an illuminating unit comprising a diffractive beam expander and an IR emitter.

Referring to FIG. 11, the width $W_{IN}$ of a collimated light beam provided by a collimating unit 310 may be expanded by a diffractive beam expander 400. An input grating 410 couples light to propagate in a waveguiding substrate 405. The output grating 420 couples light out from the substrate 405, to provide the collimated light beam LB1. The width $W_{OUT}$ of the output beam may be substantially greater than the initial width $W_{IN}$. A diffractive beam expander is described e.g. in U.S. Pat. No. 6,580,529. The collimating unit 310 comprises one or more emitters 321 and collimating optics 330.

Figure 12:
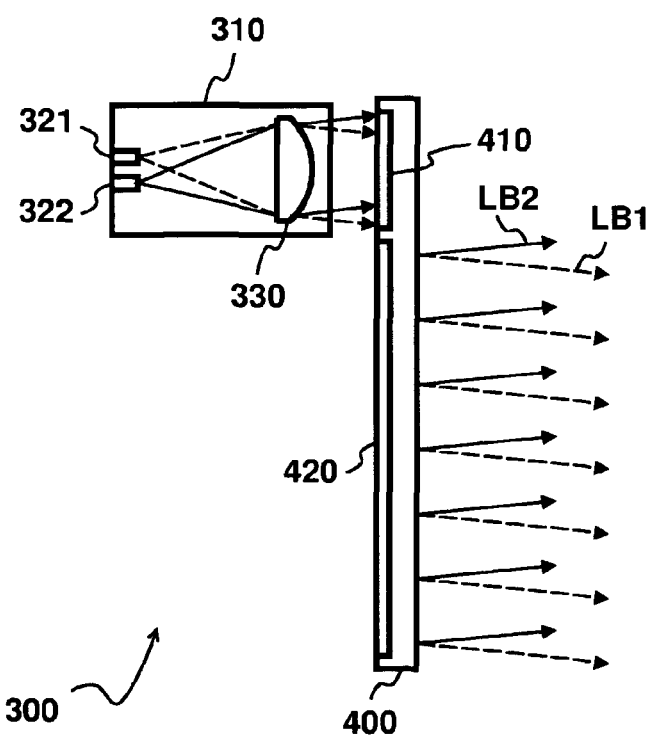
FIG. 12 shows schematically an illuminating unit comprising a diffractive beam expander and two IR emitters.

Referring to FIG. 12, two collimated light beams LB1, LB2 may be provided using a single diffractive beam expander 400.

Figure 13:
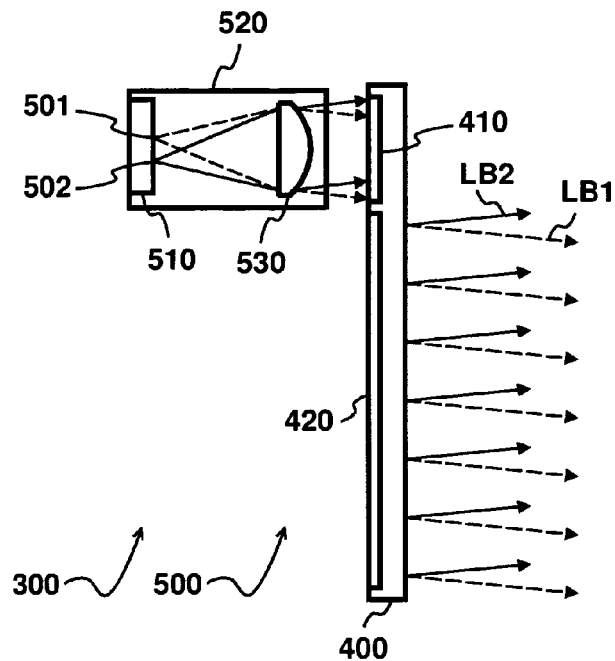
FIG. 13 shows schematically a virtual display unit comprising a diffractive beam expander.

Referring to FIG. 13, a virtual display unit 500 may comprise an optical engine 520 and a diffractive beam expander 400. The optical engine 520 comprises a micro-display 510 and viewing optics 530. The width of the viewing aperture is substantially increased by coupling the optical engine 520 to a diffractive beam expander 400.

The micro-display 510 may be an array of light emitting diodes (LED), a liquid crystal array (LCD), or a micromechanical mirror device (MEMS).

A real image formed by the pixels of the micro-display 510 is converted to a virtual image by the viewing optics 530. Each point of the micro-display 510 corresponds to a collimated beam of light transmitted from the output grating 420. Thus, the eye 100 of the observer sees a virtual image at a great or at an infinite distance.

The virtual display unit 500 may also act as the illuminating unit 300. Predetermined pixels 501, 502 of the micro-display may be used to provide the substantially collimated and modulated light beams LB1, LB2. The pixels 501, 501 may be modulated such that the light of the beams may be distinguished from other light. The pixels 501, 502 may be IR-emitting.

Figure 14:
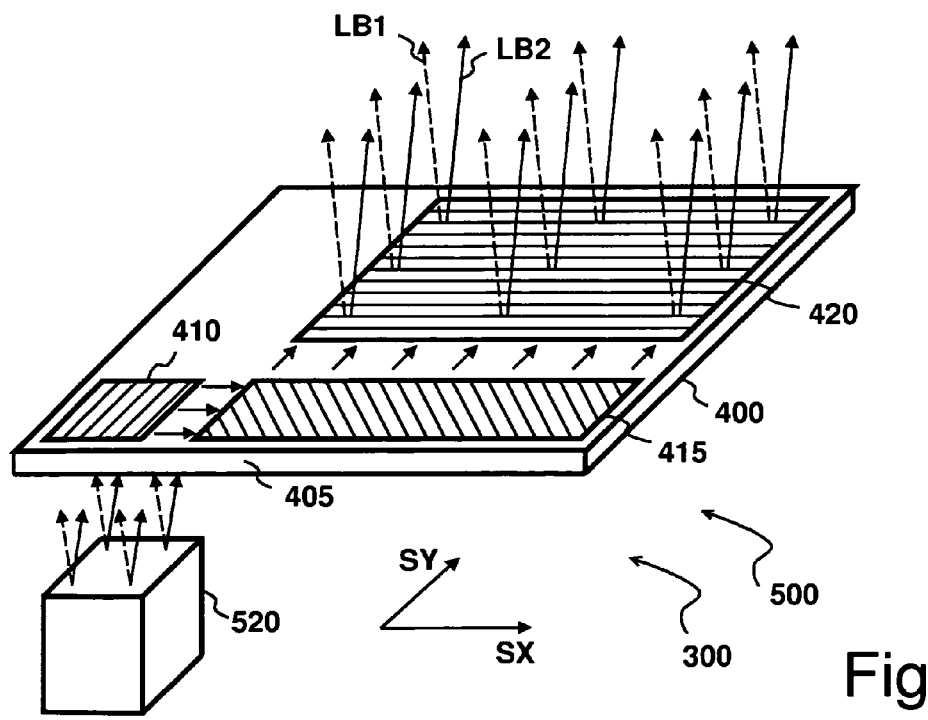
FIG. 14 is a schematic three-dimensional view of a virtual display unit comprising a diffractive beam expander.

Referring to FIG. 14, the diffractive beam expander comprises typically three gratings 410, 415 and 420. The input grating 410 couples light into the waveguiding substrate 405. The intermediate grating 415 provides beam expansion in a first direction SX. The output grating 420 provides beam expansion in a second direction SY and couples the light beams LB1, LB2 out from the diffractive beam expander 400. The output grating 420 acts also as the viewing aperture for the virtual image displayed by the optical engine 520.

When using planar diffraction gratings 410, 420, the virtual image is formed at infinite distance. However, the distance between the virtual image and the observer may also be shorter than infinity. Said distance may be, for example in the range of 1 to 2 meters. Distances shorter than infinity may be implemented using a curved diffractive beam expander disclosed in a patent application PCT/IB2004/004094. Said diffractive beam expander comprises at least one non-planar diffractive element having finite curvature radius.

Figure 15:
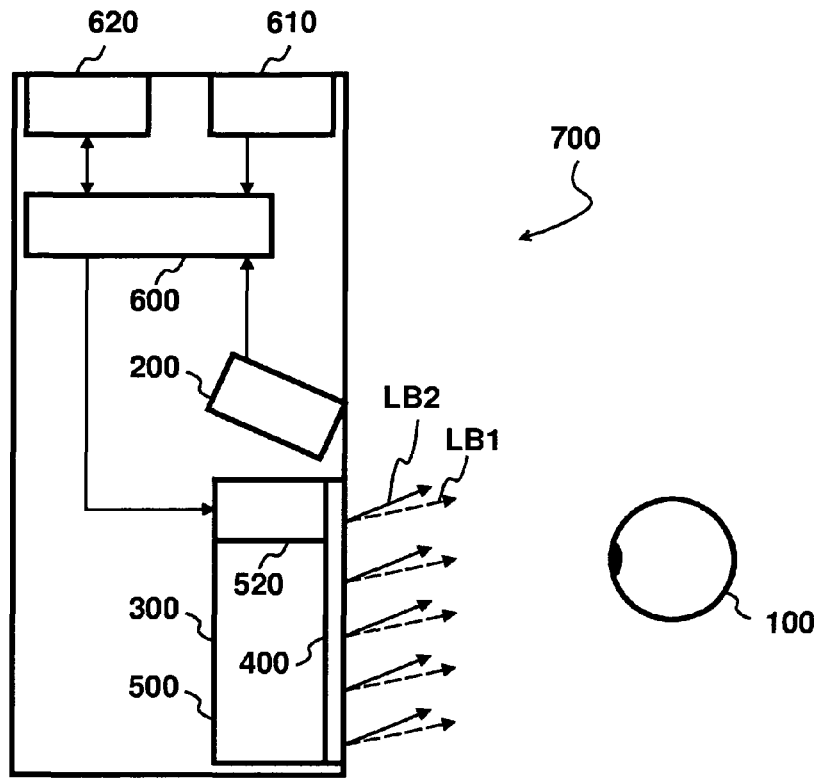
FIG. 15 shows schematically an eye tracking device comprising a virtual display.

Referring to FIG. 15, an eye tracking device 700 may comprise:

an illuminating unit 300 to provide the substantially collimated light beams LB1, LB2,
a virtual display unit 500,
an imaging unit 200,
data processing unit 600,
command interface 610, and
communications unit 620.

The command interface 610 may be a push-button device, joystick or keyboard, which allows a user to send commands to the device 700. The command interface 610 may also be a voice command device or a gesture recognition device. The communications unit 620 may be an interface module for communicating with a computer or mobile device. The communications unit 620 may also be an optical or radio frequency transmitter/receiver, which allows communication via internet or radio network.

Figure 16:
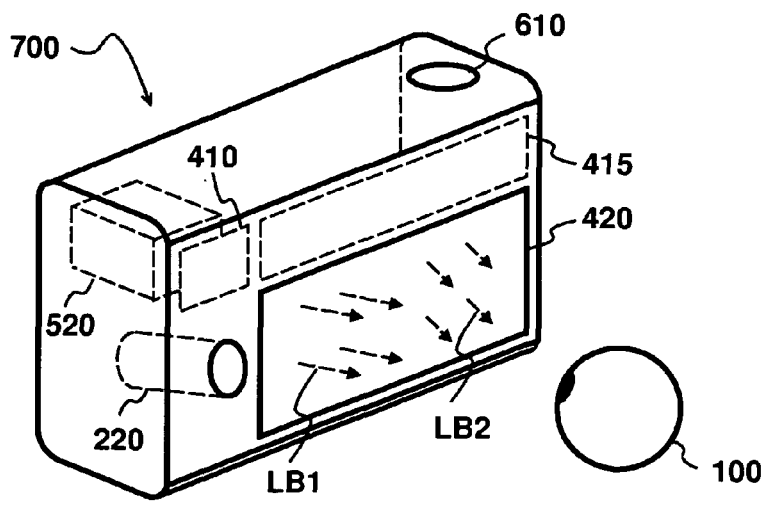
FIG. 16 is a schematic three-dimensional view of an eye tracking device comprising a virtual display.

Referring to FIG. 16, the eye tracking device 700 may be a compact, portable and lightweight device.

Figure 17:
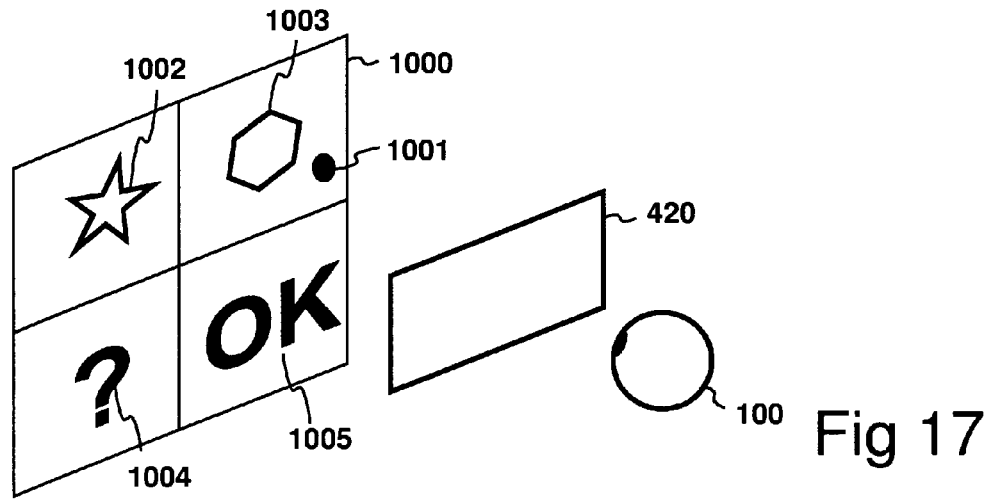
FIG. 17 shows schematically a virtual image viewed through an exit aperture.

Referring to FIG. 17, the eye 100 of the user may view a displayed virtual image 1000 through the output aperture of a virtual display, e.g. through the output grating 420 of the diffractive beam expander.

The virtual image 1000 may comprise displayed objects 1002, 1003, 1003, 1005, for example a star 1002, a hexagon 1003, a symbol "OK" 1005 and a question mark "?" 1004.

The objects or the locations of the virtual image 1000 are advantageously associated with gaze directions. Thus, when the eye 100 is looking at an object or location decided by the user, it can be determined on the basis of the gaze direction which object or location the eye is looking at. Further, each object or location may be associated with an option, and the user may select an option by looking at the respective object or location. The user may confirm the selection e.g. by pushing a button of the command interface 610 (FIGS. 15 and 16). The user may also confirm the selection by blinking his eye, or by staring at a predetermined object or location for an extended period.

For example, the user may choose between options represented by the object 1002 (star) or the object 1003 (hexagon), by directing his gaze. If the hexagon 1003 is chosen it may provide visual feedback by blinking after the selection. The user may confirm the selection e.g. by looking at the symbol "OK". Yet, the user may ask for further information by looking at the question mark "?".

The objects 1002, 1003, 1004, 1005 of the virtual image 1000 may be associated with the gaze directions in the software and/or hardware level e.g. by converting the pixel coordinates of the objects into angular coordinates. The angular coordinates of a displayed object may be compared with the gaze direction to determine whether the user is looking at said object or not.

A visible or invisible cursor 1001 may be adapted to move over the virtual image 1000, following the determined gaze direction of the eye 100. The cursor 1001 helps the user to understand that the tracker device 700 is really following his gaze. In other words, the cursor 1001 provides visual feedback to the user.

The detected gaze direction may be calibrated e.g. by moving a blinking cursor 1001 over the virtual image 1000, and asking the user to look at the cursor 1001. Further, the user may be asked to push the button of the command interface 610 when he is actually looking at the cursor 1001.

Figure 18:
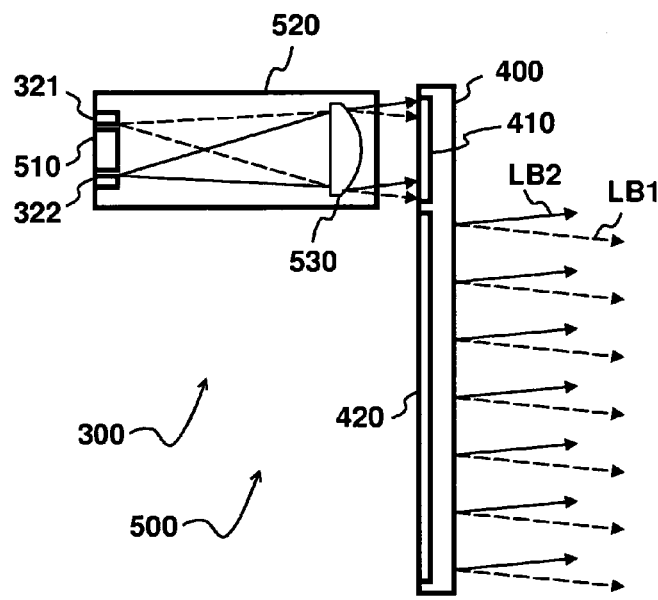
FIG. 18 shows schematically a virtual display unit comprising further IR emitters.
Figure 19:
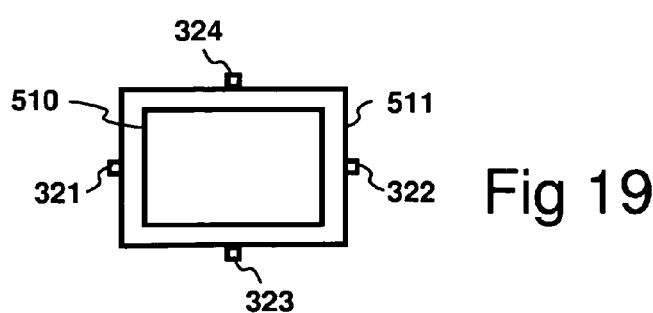
FIG. 19 shows, by way of example, the positioning of IR emitters with respect to a micro-display.

Referring to FIGS. 18 and 19, two or more infrared (IR) light emitters 321, 322 may be attached near the micro-display 510 of a virtual display unit 500. Thus the virtual display unit 500 may also act as the illuminating unit 300, providing two or more substantially collimated light beams LB1, LB2.

FIG. 19 shows, by way of example, the positioning of the IR emitters 321, 322, 323, 324 with respect to the frame 511 of the micro-display 510. By using this arrangement, the illumination unit 300 may provide three, four or more substantially collimated light beams, which propagate in different directions. The third beam and the further beams propagate in a direction which are out of the plane defined by the directions of the first beam LB1 and the second beam LB2. The use of three or more beams may provide improved accuracy. The curvature, i.e. radius of the eye 100 may be different in the vertical and horizontal directions. Thus, the use of three or more beams may allow correction of the error arising due to the non-spherical form of the eye 100.

Figure 20:
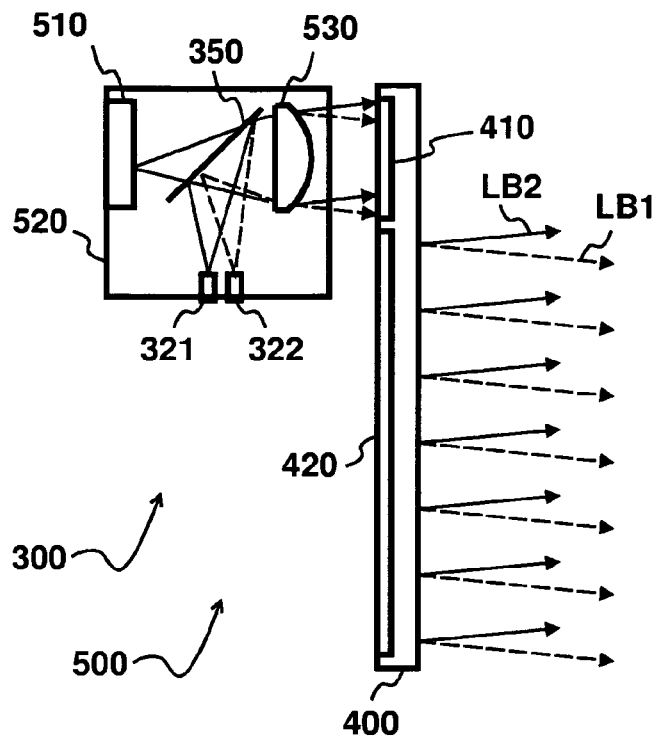
FIG. 20 shows schematically a virtual display unit comprising further IR emitters and a half-mirror.

Referring to FIG. 20, the light from infrared (IR) light emitters 321, 322 may be combined with the light emitted from the micro-display 510 by a half mirror 350. The half-mirror 350 may be a dichroic mirror which transmits visible light and reflects IR. The half-mirror 350 may be a semitransparent mirror or a polarizing mirror.

Figure 21:
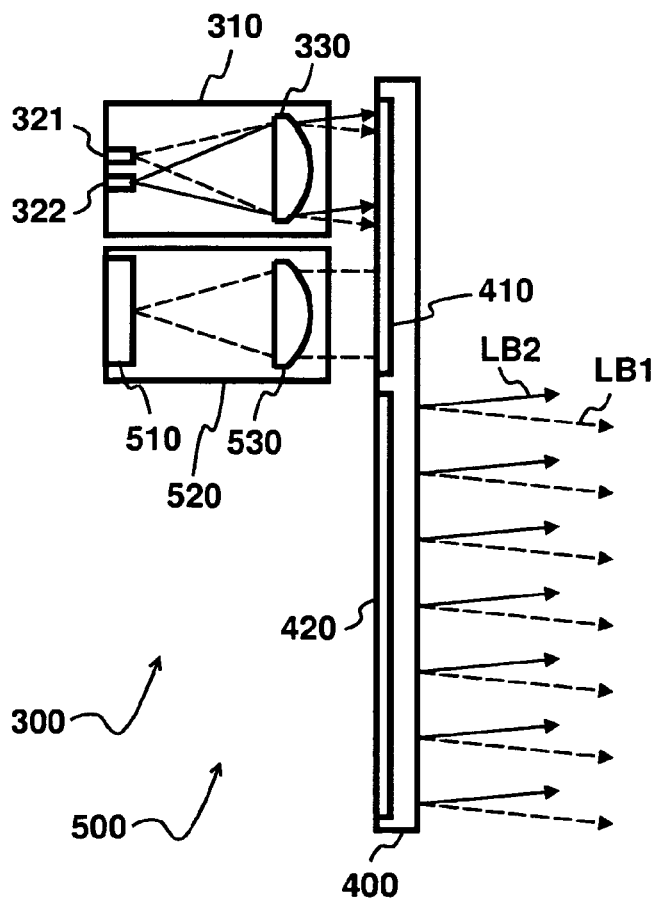
FIG. 21 shows schematically the coupling of an optical engine and an illuminating unit to a diffractive beam expander.

Referring to FIG. 21, the optical engine 520 and the collimating unit 310 may be coupled side by side to the same diffractive beam expander 400.

Figure 22:
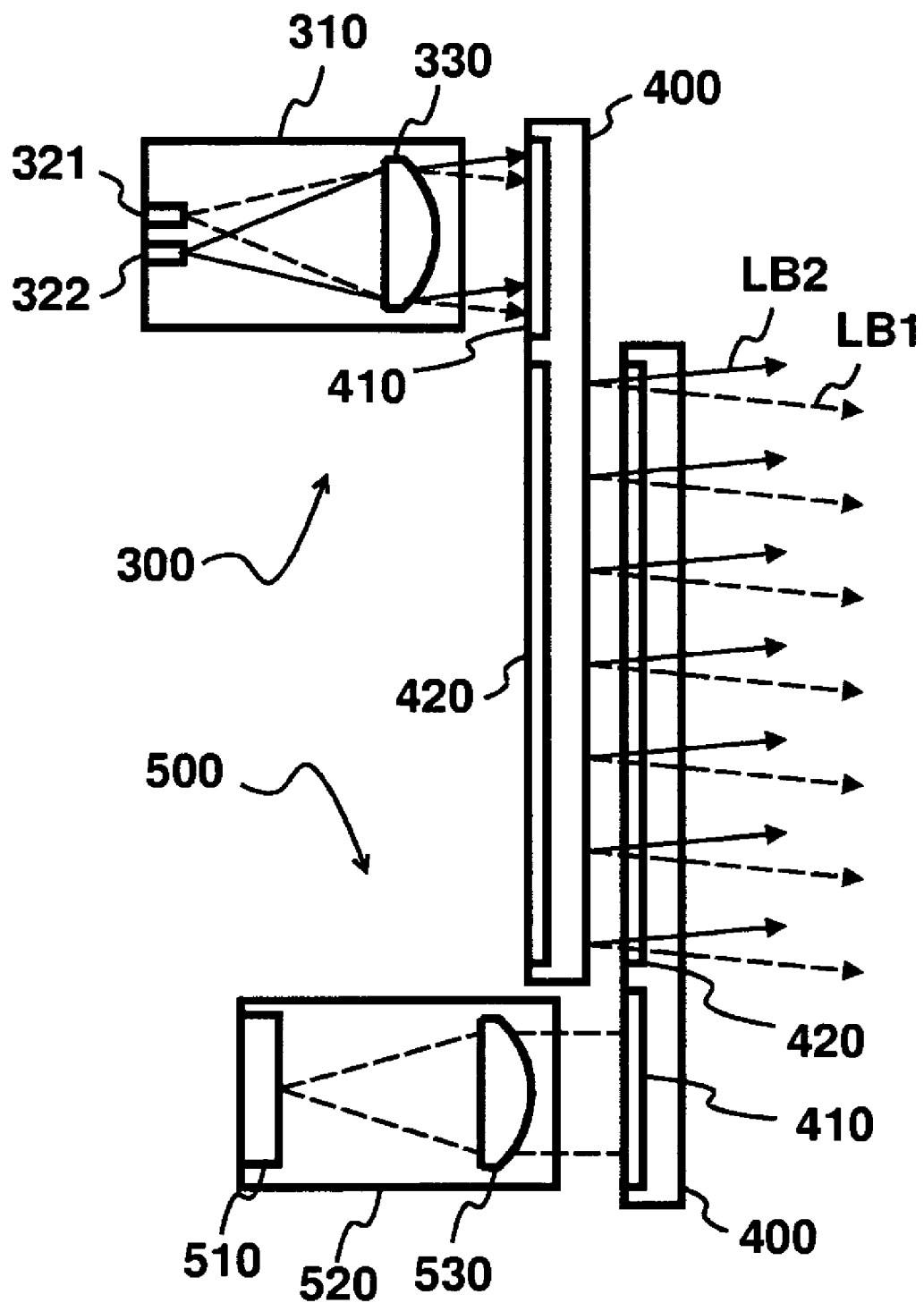
FIG. 22 shows schematically two stacked diffractive beam expanders, one displaying a virtual image and the other providing IR beams.

Referring to FIG. 22, the diffractive beam expanders 400 may be stacked such that light emitted by a first expander is transmitted through a second at least partially transparent expander. The first expander may emit visible light and the second expander may emit IR light.

Figure 23:
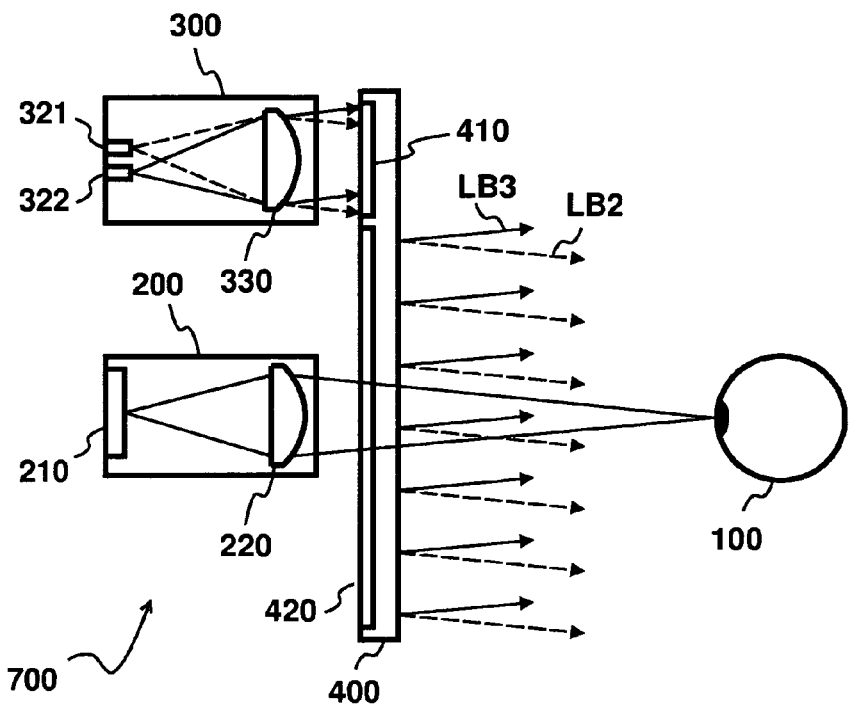
FIG. 23 shows schematically an imaging unit adapted to monitor the eye through a diffractive beam expander.

Referring to FIG. 23, the diffractive beam expander 400 may be partially transparent. The imaging unit 200 may be adapted to monitor the eye 100 through the diffractive beam expander 400.

Figure 24:
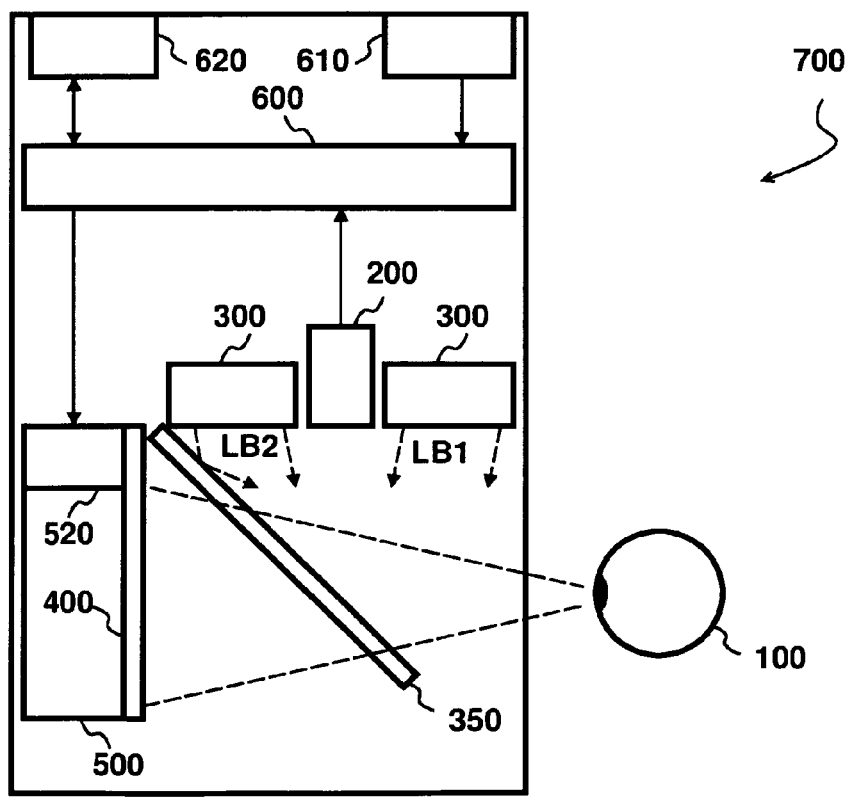
FIG. 24 shows schematically an eye tracking device comprising a virtual display, diffractive beam expander, and a half-mirror.

Referring to FIG. 24, an eye tracker device 700 may comprise a half-mirror 350 to combine the light emitted by the virtual display unit 500 with the light beams LB1, LB2 provided by the one or more illuminating units 300. The virtual display unit 500 may comprise a diffractive beam expander 400. Also the illuminating units 300 may comprise diffractive beam expanders 400. The tracker device 700 may further comprise a data processing unit, command interface 610, and communications unit 620.

Figure 25:
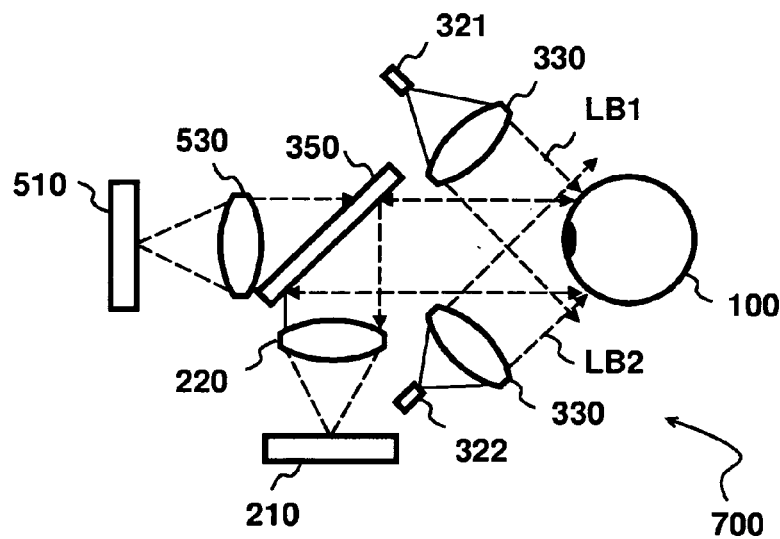
FIG. 25 shows schematically an eye tracking device comprising a virtual display and a half-mirror.

Referring to FIG. 25, an eye tracker device 700 may comprise a half-mirror 350 to combine the light emitted by the virtual display unit 500 with the collimated light beams LB1, LB2. The virtual image and the collimated light beams LB1, LB2 may be provided using the lens optics 530, 220, 330 only, i.e. without using diffractive beam expanders.

Figure 26:
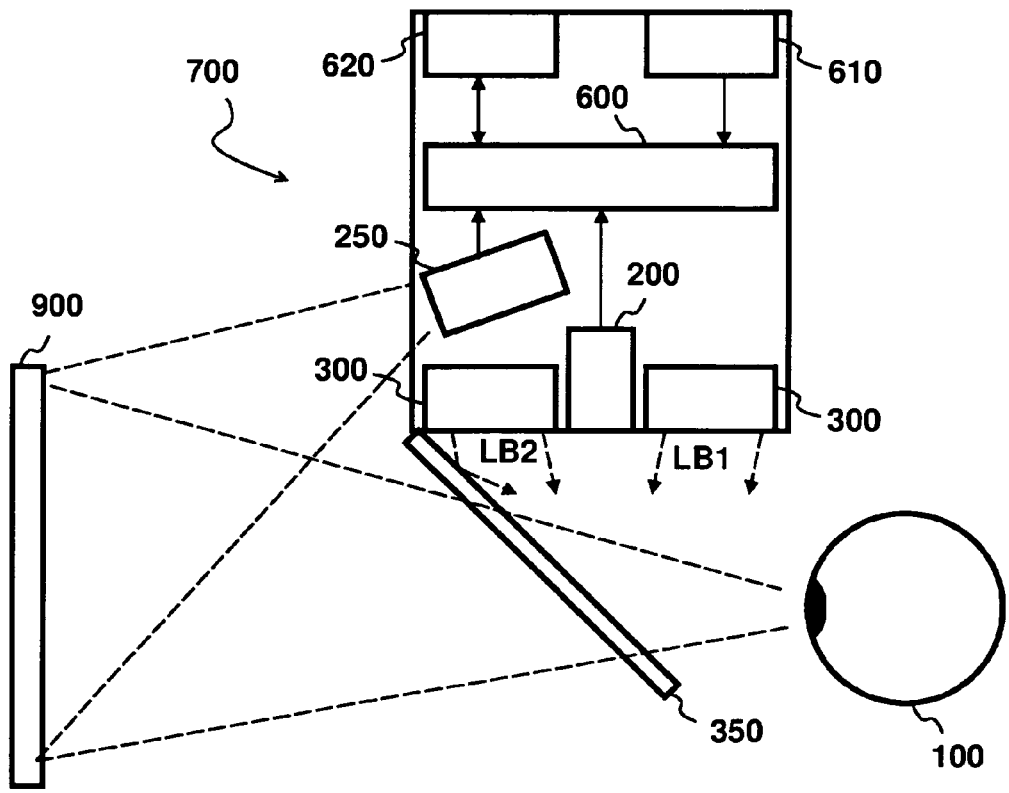
FIG. 26 shows schematically an eye tracking device comprising a half-mirror, a remote display being viewed through said half-mirror.

Referring to FIG. 26, the user may also look at a remote display screen 900. The light emitted from the remote screen 900 may be combined with the collimated light beams LB1, LB2 using a half-mirror 350. The eye tracker device 700 may further comprise a data processing unit, a command interface 610, and communications unit 620. The position of the tracker device 700 may be fixed with respect to the remote screen 900.

Alternatively, the tracker device 700 may comprise a further imaging unit 250 to monitor the angular position of the remote screen 900 with respect to the tracker device 700. That information is needed to associate the gaze direction with a location on the remote screen 900. The further imaging unit 250 may also be adapted to monitor the angular positions of the objects displayed on the screen 900, with respect to the tracker device 700.

Instead of the half-mirror, the user may also look at the screen 900 through a beam expander 400, which is transparent in the visible range of wavelengths.

Figure 27:
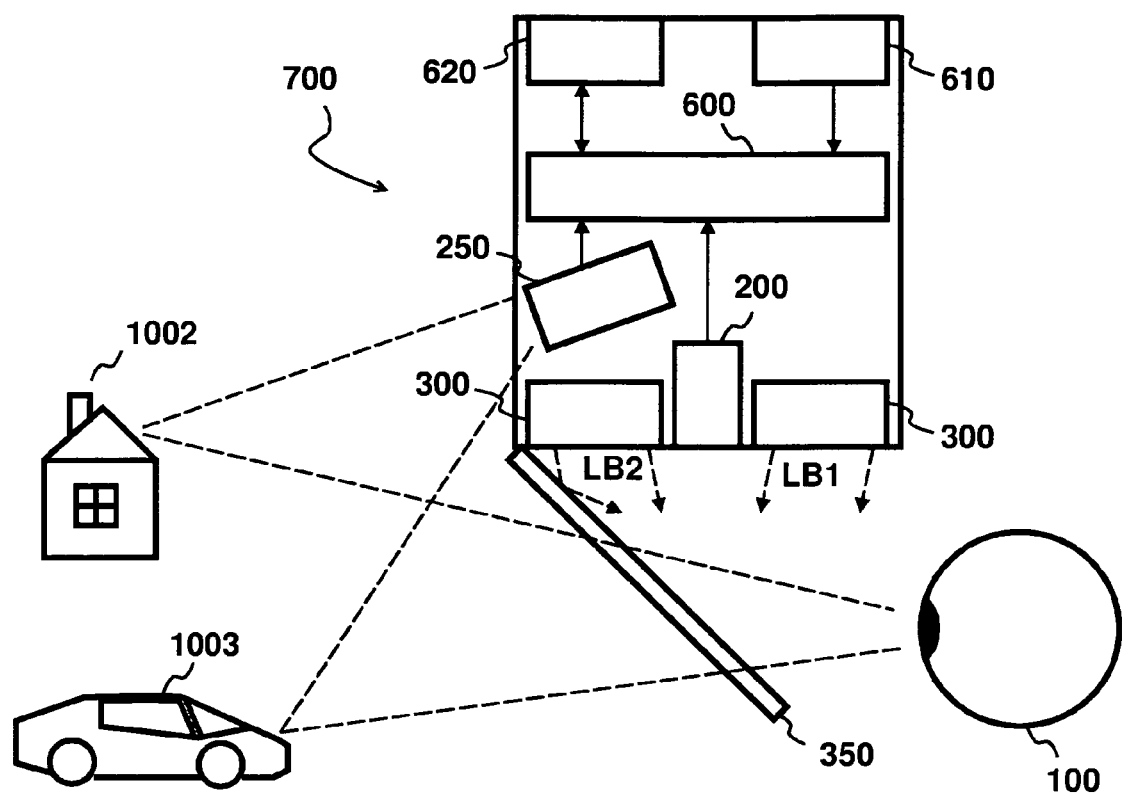
FIG. 27 shows schematically an eye tracking device comprising a half-mirror, real objects being viewed through said half-mirror.

Referring to FIG. 27, the user may also view physical objects 1002 (a house), 1003 (a car) through the half-mirror 350. The position of the tracker device 700 may be fixed with respect to the objects, or it may comprise a further imaging unit 250 to monitor the angular positions of the objects with respect to the tracker device 700. Thus, the objects, the locations of the objects, and/or the features of the landscape may be associated with the gaze directions. For example, it may be determined whether the user is looking at the house 1002 or the car 1003. Further, the objects 1002, 1003 may be associated with options such that an option may be selected by looking at the respective object.

Figure 28:
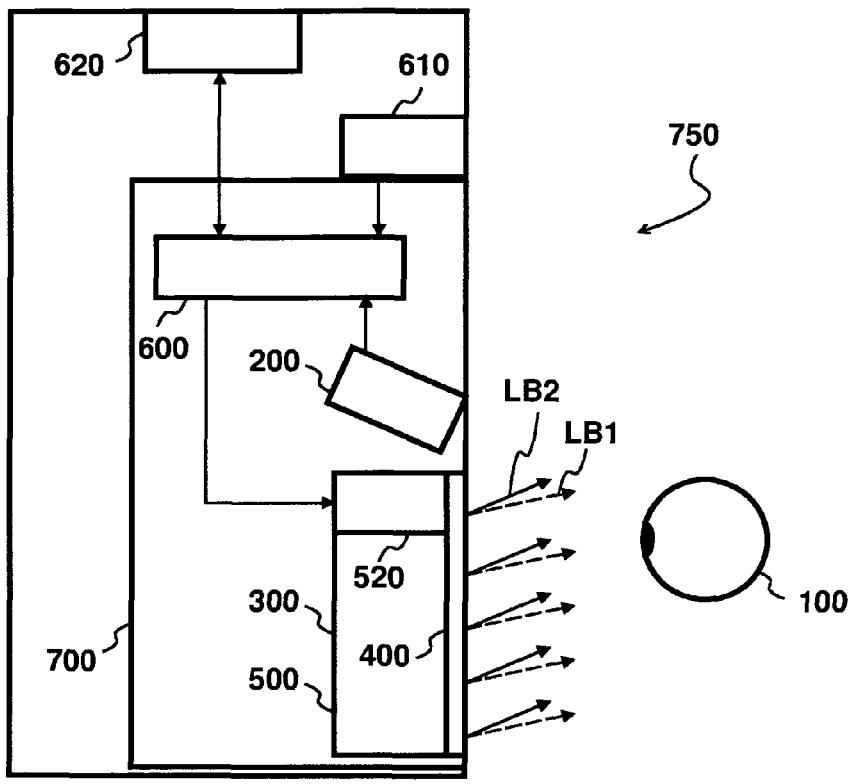
FIG. 28 shows schematically a portable device comprising an eye tracker device.

Referring to FIG. 28, a portable device 750 may comprise an eye tracker device 700.

The distance between the eye 100 and the tracker device 700 may be smaller than or equal to 0.2 m. The width of the collimated light beams LB1, LB2 may be greater than or equal to 20 mm to allow freedom to move the tracker device 700 with respect to the eye 100. The width of the collimated light beams LB1, LB2 may also be greater than or equal to 10 cm. The diffractive beam expander allows implementation of wide beams without considerably increasing the size and weight of the device 700.

Figure 29:
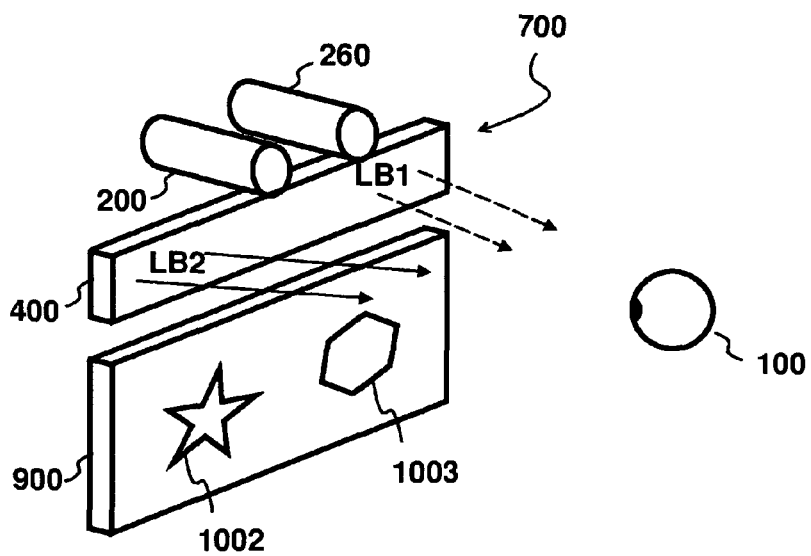
FIG. 29 is a schematic three-dimensional view of an eye tracking device which is used as a desktop device.

Referring to FIG. 29, the eye tracker device 700 may also be used as a desktop device. The eye tracker device 700 may be adapted to monitor the eye 100 at a distance, which is for example, in the range of 0.5 to 1 meters from the eye 100. The user may look at objects 1002, 1003, which may be images displayed on a display screen 900 or real physical objects.

The determined gaze direction may be associated with one of the objects 1002, 1003 when the gaze direction information is combined with the position of the eye 100 with respect to the tracker device 700. The associating can not be made only on the basis of the gaze direction unless the objects 1002, 1003 are far away when compared with the distance between the eye 100 and the tracker device 700. Also the position of the eye 100 may be needed in order to make the associating. The horizontal position and the vertical position of the eye, as well as the distance of the eye 100 from the tracker device 700 may be determined by using distance information provided by a distance monitor 260 and analyzing the image provided by the imaging unit 200. The distance monitor may be e.g. an optical distance meter. The position information may also be obtained by using two imaging units, and by determining the distance, horizontal position and vertical position by triangulation on the basis of the images of the eye acquired by said imaging units.

The eye 100 of the user may view one of the objects 1002, 1003. The gaze direction information together with the pixel coordinates of the objects and the position of the eye 100 is used to determine which object the user is looking at, e.g. whether the user is looking at the star 1002 or the hexagon 1003 displayed on the screen 900.

When used as a desktop device, the tracker device 700 may comprise one or more beam expanders 400 which have a large output aperture in order to allow for the user adequate freedom to move his head. Alternatively, the tracker device 700 may comprise means to change the directions of the collimated beams LB1, LB2 such that they impinge on the user's eye 100 when the user moves his head. The information needed for following the head's movements may be obtained e.g. by analysis of the image provided by the imaging unit 200.

The eye tracker device 700 may be, may be a part of, or may be used in combination with a device selected from the following list: a portable device, device with wireless telecommunicating capabilities, imaging device, image scanner, digital camera, mobile phone, gaming device, music recording/playing device (based on e.g. MP3-format), remote control transmitter or receiver, wrist watch, compass, heartbeat monitoring device, medical instrument, appliance for disabled persons, measuring instrument, industrial measuring instrument, process control device, target finding device, aiming device, navigation device, personal digital assistant (PDA), communicator, portable internet appliance, and hand-held computer. The eye tracker device 700 may comprise a battery, telecommunicating unit, audio devices and/or data storage units. The eye tracker device 700 may be attached to a headgear, cap or helmet.

The method according to the present invention may also be implemented by using a computer program product. Raw data may be provided by a system comprising the imaging unit 200 and means to provide the collimated light beams LB1, LB2. The raw data may comprise the whole image 201 of the eye 100 or only the coordinates of the reflection spots G1, G2 and the pupil P. The computer program product comprises computer program code sections stored in a readable medium, which when executed by a processor 600, determine the gaze direction on the basis of the data and the directions of the light beams LB1, LB2.

The computer program product may be e.g. a CR-ROM disc, or a memory card comprising said program. The computer program code sections of the product may be downloadable from internet websites. The computer program may be installed e.g. in a portable computer which is connected to an imaging unit 200.

The user interface of e.g. a computer or a mobile device may be based partly or completely on the tracking of the gaze direction. The user may give commands at a high rate by directing his gaze. For example, text may be written and processed by selecting displayed letters, words or entire sentences by the gaze.

When the tracker device 700 is attached to a headgear, the gaze direction information may be combined with further information regarding the position and/or the orientation of the head with respect to the environment. The position of the head with respect to the environment may be determined e.g by using a GPS (Global Positioning System) navigation system, a compass and/or a reference beacon adapted to send ultrasound, infrared or radio frequency tracking signal.

The eye tracker device 700 may be adapted to display virtual images such that the user may view displayed virtual images and also real physical objects substantially simultaneously. That kind of a tracker device 700 may be used as a part of an augmented reality system.

The eye tracker device 700 may be in coupled to a remote computer. The signal processing associated with the determination of the gaze direction may be performed in a remote computer or data processing unit.

The virtual display unit may be used to display moving or still images, e.g. a movie, photographs, www-pages, diagrams and/or text.

The illuminating units 300 may also be implemented using light sources, e.g. lasers, which inherently emit collimated light beams.

The beam expanders may be based on diffractive optics, on lens combinations, on stacked prisms and/or on stacked half-mirrors.

The diffractive beam expander 400 may be implemented using periodic surface relief patterns. The diffractive beam expander 400 may also be a holographic diffractive beam expander, comprising periodic variations of refractive index, implemented by holographic manufacturing techniques.

A patent application US2004/0062502 discloses a beam expander with one or more surface interfaces to improve color uniformity in the beam expander, e.g. when expanding red, green and blue light beams simultaneously.

A patent application PCT/FI2003/000948 discloses a split diffractive grating element to balance diffraction efficiency with respect to variations in the angle of incidence. Said element may be used in the diffractive beam expander 400.

The micro-display 510 may be a reflective, emissive or transmissive two-dimensional light-modulating array. The micro-display 510 may be an array of light emitting diodes (LED, Organic Light Emitting Diode), an array of micromechanical mirrors (MEMS display), or an array of liquid crystal cells (liquid crystal on silicon). The micro display 510 may also be implemented using opto-mechanically scanned light beams, e.g. using a modulated light beam, which is deflected and/or shifted by rotating mirrors.

The eye tracker device 700 may comprise two adjacent virtual displays, one for the left eye and one for the right eye. The virtual displays may be separately controlled to display three-dimensional virtual images. When a person is looking at a displayed three-dimensional image, the difference between the gaze direction of the left eye may and the gaze direction of the right eye may be used to provide distance information related to said image.

The eye tracker device 700 may be adapted to monitor the gaze direction of the left and right eyes separately. When the user is looking at a remote object, the difference between the gaze direction of the left eye may and the gaze direction of the right eye may be used to provide distance information related to said object. This embodiment may be used in augmented reality applications.

For the person skilled in the art, it will be clear that modifications and variations of the devices and method according to the present invention are perceivable. The particular embodiments described above with reference to the accompanying drawings are illustrative only and not meant to limit the scope of the invention, which is defined by the appended claims.

What is claimed is:

1. A device for detecting gaze direction of an eye, said device comprising:
    a first imaging unit to acquire an image of said eye,
    at least one illuminating unit to provide a first substantially collimated light beam and a second substantially collimated light beam, said collimated light beams having different directions with respect to said device such that said first collimated light beam provides a first reflection spot when light is reflected from the surface of the eye and that said second collimated light beam provides a second reflection spot when light is reflected from the surface of the eye, said reflection spots appearing in said image,
    a data processing unit to determine the gaze direction of the eye with respect to said device based on the position of said first reflection spot in said image, on the position of said second reflection spot in said image, on the position of the pupil and/or iris of the eye in said image, and on the directions of the collimated light beams, and
    one or more beam expanders to expand the width of the collimated light beams.

2. The device according to claim 1 wherein said one or more beam expander are diffractive beam expander.

3. The device according to claim 2, wherein said first imaging unit is configured to view the eye through said one or more beam expanders, which is at least partially transparent to the wavelengths of the collimated light beams.

4. The device according to claim 1 wherein said first imaging unit is configured to view the eye through said one or more beam expanders, which are at least partially transparent to the wavelengths of the collimated light beams.

5. The device according to claim 1 wherein the width of the first collimated light beam is greater than or equal to 20 millimeters.

6. The device according to claim 1 wherein said illuminating unit comprises one semiconductor device to emit invisible infrared light.

7. The device according to claim 1 further comprising a virtual display unit to display virtual images.

8. The device according to claim 1 configured to associate an object or a location with a gaze direction.

9. The device according to claim 8 further comprising a half-mirror configured to reflect or transmit said collimated light beams towards the eye, wherein it is possible for the eye to view said object and/or said location via said half-mirror.

10. The device according to claim 8 comprising a further imaging unit to monitor the angular position of said object or location with respect to said device.

11. The device according to claim 1 further comprising a command interface to send commands to the data processing unit in order to confirm a selection of an option or a target associated with the determined gaze direction.

12. The device according to claim 1 further comprising a distance monitor to determine the distance between said eye and said first imaging unit.

13. The device according to claim 1 further comprising means to change the direction of said first collimated light beam and/or the direction of said second collimated light beam with respect to said device.

14. The device according to claim 1, wherein said illuminating unit comprises pixels of a micro-display.

15. The device according to claim 1 further comprising means for sending image data to a remote data processing unit, wherein said determination is performed in the remote data processing unit.

16. A method for detecting gaze direction of an eye, said method comprising:
    directing a first substantially collimated light beam towards the eye in order to provide a first reflection spot when light is reflected from the surface of the eye,
    directing a second substantially collimated light beam towards the eye in order to provide a second reflection spot when light is reflected from the surface of the eye, said second collimated light beam having a direction different from the direction of said first collimated light beam, wherein at least one of said collimated light beams is provided using one or more beam expanders,
    acquiring an image of the eye by a first imaging unit,
    determining the gaze direction of said eye with respect to said first imaging unit based on the position of said first reflection spot in said image, on the position of said second reflection spot in said image, on the position of the pupil and/or iris of the eye in said image, and on the directions of the collimated light beams.

17. The method according to claim 16 wherein at least one of said collimated light beams is provided using one or more diffractive beam expanders.

18. The method according to claim 17, wherein acquiring an image of the eye by said first imaging unit is done through said one or more beam expanders, which are at least partially transparent to the wavelengths of the collimated light beams.

19. The method according to claim 16 wherein the width of the collimated light beams is greater than or equal to 20 mm.

20. The method according to claim 16 wherein the distance between the first imaging unit and the eye is smaller than or equal to 0.2 m.

21. The method according to claim 16 further comprising associating an object or a location with a gaze direction.

22. The method according to claim 21 further comprising determining the angular position of said object or said location with respect to said first imaging unit based on an image of said object or location acquired by a further imaging unit.

23. The method according to claim 21, wherein said collimated light beams are reflected or transmitted towards the eye using a half-mirror, wherein it is possible for the eye to view said object and/or said location via said half-mirror.

24. The method according to claim 16 further comprising:
displaying a virtual image, and
associating a location of said virtual image with a gaze direction.

25. The method according to claim 16 further comprising selecting an option or a target based on the detected gaze direction of said eye.

26. The method according to claim 16 further comprising varying the direction of said first collimated light beam and/or the direction of said second collimated light beam.

27. The method according to claim 16 wherein said first collimated beam and said second collimated beam are provided using pixels of a micro-display.

28. The method according to claim 16 wherein said first collimated beam and said second collimated beam are provided using light-emitting semiconductor devices.

29. The method according to claim 16 further comprising sending image data to a remote data processing unit, and performing said determination in the remote data processing unit.

30. The method according to claim 16, wherein acquiring an image of the eye by said first imaging unit is done through said one or more beam expanders, which are at least partially transparent to the wavelengths of the collimated light beams.

31. A portable device comprising an eye tracking device for detecting gaze direction of an eye, said tracking device comprising:
a first imaging unit to acquire an image of said eye,
at least one illuminating unit to provide a first substantially collimated light beam and a second substantially collimated light beam, said collimated light beams having different directions with respect to said device such that said first collimated light beam provides a first reflection spot when light is reflected from the surface of the eye and that said second collimated light beam provides a second reflection spot when light is reflected from the surface of the eye, said reflection spots appearing in said image,
a data processing unit to determine the gaze direction of the eye with respect to said tracking device based on the position of said first reflection spot in said image, on the position of said second reflection spot in said image, on the position of the pupil and/or iris of the eye in said image, and on the directions of the collimated light beams, and
one or more beam expanders to expand the width of the collimated light beams.

32. The portable device according to claim 31 further configured to provide wireless communication capabilities.

33. A computer readable medium stored with computer program code sections for determining the gaze direction of an eye, which when executed by a processor are for determining a gaze direction of an eye with respect to an imaging unit, said imaging unit to acquire an image of an eye, based on a position of a first reflection spot in said image, on a position of a second reflection spot in said image, on a position of the pupil and/or iris of the eye in said image, and on the directions of a first substantially collimated light beam and a second substantially collimated light beam, said collimated light beams having different directions with respect to said imaging unit such that said first collimated light beam provides a said first reflection spot when light is reflected from the surface of the eye and that said second collimated light beam provides said second reflection spot when light is reflected from the surface of the eye, said reflection spots appearing in said image, wherein at least one of said collimated light beams is provided using one or more beam expanders.

34. The computer readable medium according to claim 33, wherein said computer program code sections are for:
determining the angular position of a first reflection point and the angular position of a second reflection point on the surface of the eye based on the coordinates of said two reflection spots,
determining the direction of a first surface normal at said first reflection point and a second surface normal at said second reflection point based on the directions of said collimated light beams and the directions of a first vector and a second vector, said first vector being designated by the principal point of said imaging unit and said first reflection point, and said second vector being designated by the principal point of said imaging unit and said second reflection point,
determining a third vector which is substantially perpendicular to said surface normals,
determining the lengths of said first, second and third vector,
approximating the position of the eye center by a point on the third vector, said point being preferably the midpoint of the third vector,
determining the direction of a fourth vector based on the coordinates of the pupil and/or iris in said image, said fourth vector being designated by the principal point of said imaging unit and the pupil center,
determining the position of the pupil center, and
providing the gaze direction based on the position of said approximated eye center and said pupil center.

35. A device for detecting gaze direction of an eye, said device comprising:
means for acquiring an image of said eye,
means for providing a first substantially collimated light beam and a second substantially collimated light beam, said collimated light beams having different directions with respect to said device such that said first collimated light beam provides a first reflection spot when light is reflected from the surface of the eye and that said second collimated light beam provides a second reflection spot when light is reflected from the surface of the eye, said reflection spots appearing in said image,
means for determining the gaze direction of the eye with respect to said device based on the position of said first reflection spot in said image, on the position of said second reflection spot in said image, on the position of the pupil and/or iris of the eye in said image, and on the directions of the collimated light beams, and
one or more beam expanders to expand the width of the collimated light beams.

* * * * *

UNITED STATES PATENT AND TRADEMARK OFFICE
CERTIFICATE OF CORRECTION

| | |
|---|---|
| PATENT NO. | : 8,360,578 B2 |
| APPLICATION NO. | : 12/223245 |
| DATED | : January 29, 2013 |
| INVENTOR(S) | : Nummela |

It is certified that error appears in the above-identified patent and that said Letters Patent is hereby corrected as shown below:

In the Claims

<u>Column 13,</u>
Line 61, "expander", both occurrences, should read --expanders--.

Signed and Sealed this
Fourteenth Day of May, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,360,578 B2  
APPLICATION NO. : 12/223245  
DATED : January 29, 2013  
INVENTOR(S) : Ville Nummela Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1178 days.

Signed and Sealed this
First Day of September, 2015

Michelle K. Lee
*Director of the United States Patent and Trademark Office*